United States Patent [19]

Dalmasso et al.

[11] Patent Number: 5,788,941
[45] Date of Patent: Aug. 4, 1998

[54] METHOD OF STERILIZATION OF BONE TISSUE

[75] Inventors: Joseph P. Dalmasso, Apex; Thaddeus J. Mielnik, Raleigh, both of N.C.

[73] Assignee: Steris Corporation, Mentor, Ohio

[21] Appl. No.: 593,156

[22] Filed: Jan. 31, 1996

[51] Int. Cl.⁶ ...................................................... A61L 2/20
[52] U.S. Cl. ........................ 422/33; 435/1.1; 435/1.3
[58] Field of Search ............................ 422/33; 435/1.1, 435/1.3

[56] References Cited

U.S. PATENT DOCUMENTS

| | | |
|---|---|---|
| Re. 33,007 | 8/1989 | Bier . |
| 4,169,124 | 9/1979 | Forstrom et al. . |
| 4,554,686 | 11/1985 | Baker . |
| 4,627,853 | 12/1986 | Campbell . |
| 4,637,931 | 1/1987 | Schmitz . |
| 4,654,464 | 3/1987 | Mittelmeier . |
| 4,678,470 | 7/1987 | Nashef . |
| 4,764,351 | 8/1988 | Hennebert et al. ............ 422/33 |
| 4,789,663 | 12/1988 | Wallace . |
| 4,865,602 | 9/1989 | Smestad . |
| 4,909,999 | 3/1990 | Cummings . |
| 4,919,931 | 4/1990 | Roseberg nee Goldner . |
| 4,946,792 | 8/1990 | O'Leary . |
| 4,956,145 | 9/1990 | Cummings . |
| 5,068,087 | 11/1991 | Childers . |
| 5,120,656 | 6/1992 | O'Leary . |
| 5,286,448 | 2/1994 | Childers . |
| 5,333,626 | 8/1994 | Morse . |
| 5,445,792 | 8/1995 | Rickloff . |
| 5,460,962 | 10/1995 | Kemp . |
| 5,513,662 | 5/1996 | Morse et al. ................... 422/27 |
| 5,527,508 | 6/1996 | Childers et al. ................ 422/33 |

FOREIGN PATENT DOCUMENTS

| | | |
|---|---|---|
| 0 424 159 | 4/1991 | European Pat. Off. . |
| 584484 | 3/1994 | European Pat. Off. . |
| 39728 | 2/1964 | Germany . |
| 278815 | 5/1990 | Germany . |
| 4022986 | 1/1992 | Germany . |
| 4125776 | 2/1993 | Germany . |
| 957911 | 9/1982 | U.S.S.R. . |
| 1461473 | 2/1989 | U.S.S.R. . |
| 1768157 | 10/1992 | U.S.S.R. . |
| 181817 | 4/1993 | U.S.S.R. . |
| WO 95/19797 | 7/1995 | WIPO . |

OTHER PUBLICATIONS

Taber's Cyclopedic Medical Dictionary, 14th Ed., C.L. Thomas (ed.), F.A. Davis, Philadelphia, pp. 177–178.
White, A., Handler, P., & Smith, E.L., Principles of Biochemistry, 4th Ed., McGraw–Hill, New York, pp. 890–891.
Todd–Sanford, Clinical Diagnosis by Laboratory Methods, 14th ED., Davidsohn & Henry (eds)., W.B. Saunders, Philadelphia, p. 572.

Primary Examiner—Jay H. Woo
Assistant Examiner—Betsey J. Morrison
Attorney, Agent, or Firm—Fay, Sharpe, Beall, Fagan, Minnich & McKee

[57] ABSTRACT

The invention is directed to the sterilization of bone tissue for transplantation employing a hydrogen peroxide vapor sterilant. The bone tissue is exposed to the sterilant vapor at a pressure, temperature, and concentration, and for a period of time that is sufficient to sterilize the bone tissue, but insufficient to cause substantial physical, chemical and biological damage. The bone tissue is defatted, preferably demineralized, substantially free of moisture and blood, and may be lyophilized prior to sterilization.

19 Claims, No Drawings

METHOD OF STERILIZATION OF BONE TISSUE

BACKGROUND

Transplantation or grafting of bones and bone products has become a relatively widely utilized medical procedure. In addition to whole bones, the range of bone products used for transplantation includes bone chips for surgical procedures, such as spinal fusion and craniotomies, bone dust (powder) used in dental repair and/or reconstruction, glutaraldehyde-tanned bone, demineralized bone, purified collagen preparations and ossein hydroxyapatite compounds. Bones for transplantation may be obtained from autologous, allogeneic or xenogeneic sources.

In the various processes used to prepare bone and bone products for clinical use in transplantation, it is frequently desirable or necessary to include a preliminary decontamination step and/or a final product sterilization step to inactivate a wide range of potentially infectious agents, including bacteria, viruses, yeasts and fungi, which are common flora in humans and animals, and in a hospital environment. Preliminary decontamination, such as the treating of fresh or frozen bone with disinfectants and/or broad spectrum antibiotic solutions, is generally employed to substantially disinfect or decontaminate the bone prior to product-forming processing steps. Following the optional preliminary decontamination, the steps for processing bones generally include debridement, shaping and cutting, cleaning, pulverizing (if desired), defatting, and demineralization.

After the final bone product is formed, it is preferably sterilized, i.e. to a sterility assurance level of $10^{-6}$, prior to its preservation by lyophilization, cryopreservation or fresh freezing. The most frequently used methods for final product sterilization include exposure to high temperature (e.g. boiling), high doses of gamma radiation or high concentrations of ethylene oxide gas. Such high temperature and high-dose toxic sterilization techniques, however, can destroy or impair the biological properties of the bone tissue by denaturing essential proteins, and can cause disruption of the collagen matrix cross-linkage that is important to mechanical strength. For example, doses of gamma radiation of as much as 3-4 Mrads may be required to produce sterility in bone products. This dose is far greater than the 2 Mrads which may cause undesirable excessive cross-linkages in collagen. Similarly, the high doses of ethylene oxide required to achieve sterilization may lead to irreversible alkylation of the proteins and/or factors which are present in the bone product to be implanted, and which are necessary for in vivo bone regeneration after implantation (e.g. bone morphogenetic proteins and/or osteogenesis factors). Preservation of such proteins, which reside naturally in bone tissues and are present in preparations of demineralized bone and in certain collagen preparations used in the construction of implants, is essential if inductive repair of bone is desired. Alternatively, preservation of these proteins is not essential when employing implants, such as glutaraldehyde-tanned bone or hydroxyapatite preparations, which may provide only structural and matrix support for conductive bone repair.

A further disadvantage of the use of ethylene oxide for sterilization of bone tissue for transplantation is that ethylene oxide is considered to be carcinogenic. Additionally, long periods of aeration after sterilization are required to remove residual sterilant from the sterilization chamber and the bone tissue in order to eliminate a potential health hazard to health care workers and the transplant recipient, thus lengthening the period of time of unavailability of the bone tissue for transplant.

There is, therefore, a need for a method of final product sterilization, which can produce a sterility assurance level of at least $10^{-6}$, and which will not cause substantial damage to the chemical, biological or physical characteristics of bone tissue. Preferably, such a sterilization procedure can be easily integrated into existing product-preparation processes, and also improve sterilization and aeration times compared with existing methods. Such a sterilization procedure should preferably be suitable to be utilized for a substantial number of different bone tissue products currently employed in transplantation.

SUMMARY OF THE INVENTION

The present invention is a method of sterilization of bone tissue employing a sterilant comprising hydrogen peroxide vapor. The method is suitable for final sterilization of a wide variety of bone products for transplantation, such as whole bone, sections of bone, bone chips, bone dust (powder) and tanned bone which, during processing, have been defatted and, preferably, demineralized, and which are also substantially free of moisture and blood or bone marrow. The method may also be useful for sterilization of products comprising a bone tissue, such as collagen preparations, that are free of the mineral components of bone.

The method is particularly suitable for sterilization of bone tissue which has been lyophilized, where the lyophilization chamber may also serve as the sterilization chamber, and the final sterilization process may be easily integrated into existing product-preparation processes.

In accordance with the present invention, a bone tissue, which has preferably been substantially demineralized and defatted and is substantially free of moisture and blood, is placed into a sterilization chamber. The tissue is then exposed to a sterilant comprising hydrogen peroxide vapor at a pressure, temperature, and concentration, and for a period of time sufficient to sterilize the bone tissue, but insufficient to cause substantial physical, chemical and biological damage to the bone tissue. Residual hydrogen peroxide vapor is then removed from the chamber and the bone tissue by known methods.

The method may be practiced with any sterilization system or sterilization cycle that employs a sterilant comprising hydrogen peroxide vapor. Such sterilization systems may include cycles employing the sterilant vapor in a deep vacuum cycle, the sterilant vapor including a flow-through component comprising an inert carrier gas at, or slightly above or below, atmospheric pressure, and combinations thereof.

The invention may be practiced in any sterilization chamber, including lyophilizers and isolation chambers. If a lyophilizer is the sterilization chamber, the vacuum drawn in the lyophilization chamber may also serve to dry the product prior to exposure to hydrogen peroxide vapor. When used in sterilization systems at or near atmospheric pressure, the method of the invention may be employed to sterilize the cortical layers of bone, such as femoral heads, the surfaces of which are substantially moisture-free and blood-free, but have not been substantially defatted or had bone marrow removed.

Sterilization of bone tissue with a sterilant comprising hydrogen peroxide is advantageous compared with previous methods. For example, compared with ethylene oxide sterilization, sterilization with hydrogen peroxide vapor takes place at lower temperatures, and exposure times and aeration times are significantly shorter. Additionally, the chemical nature of the hydrogen peroxide sterilization process does not substantially harm the chemical, biological or physical characteristics of the bone tissue, and essential proteins are thus preserved.

DETAILED DESCRIPTION OF THE INVENTION

The present invention provides a method of sterilizing bone tissue by exposure to a sterilant comprising hydrogen peroxide vapor. The word sterilization, for purposes of this invention, is used to indicate that the bone tissue has been rid of substantially all bacteria, viruses, yeasts and fungi, to a sterility assurance level of at least $10^{-6}$.

The method of the invention is suitable for, but not limited to, sterilization of cortical and cancellous bone tissue, whether the tissues be represented by whole bones, sections of whole bone, bone chips, bone powder, tanned bone, collagen preparations, or mixtures thereof. For the purposes of this invention, the term "bone tissue" is used to encompass all of the aforementioned bone products, whether human or animal, unless stated otherwise.

In order to be able to appreciate the advantages and limitations of the method of the invention, a brief description of bone tissue to be sterilized by the hydrogen peroxide vapor of the invention is here provided.

Both cortical and cancellous bone tissue are present in the donor long bones most frequently utilized for transplantation purposes, such as the tibia, humerus, femur, radius and ulna. As defined in *Taber's Cyclopedic Medical Dictionary*, page 198, compact (cortical) bone tissue is "dense, hard bone with microscopic spaces" which forms the outer wall of long bones. Cancellous bone is defined as "a spongy bone in which the matrix forms connecting bars and plates, partially enclosing many intercommunicating spaces filled with bone marrow". The bone marrow found in cancellous bone tissue comprises mainly red marrow containing hematopoietic (blood forming) cells. Yellow marrow, found in the medullary (marrow-containing) canal, principally comprises fat cells and connective tissue.

The average long bone contains, by volume, about 75% inorganic mineral salts and approximately 25% organic matrix. The mineral portion of bone largely comprises hydroxyapatite, a naturally occurring form of calcium phosphate, and other cations and anions, such as magnesium, potassium, sodium, fluoride, carbonate, hydroxide and citrate. If bone is treated with, for example, a dilute acidic solution, the mineral portion dissolves, leaving a flexible, tough, nearly translucent organic matrix, consisting largely of collagen, which retains the shape of the intact bone.

The bone tissue to be sterilized by the method of the present invention is preferably demineralized prior to exposure to a sterilant comprising hydrogen peroxide vapor, since hydrogen peroxide is known to be reactive with some cations and anions of the mineral portion of bone. Bone tissue which has not been demineralized may be sterilized with hydrogen peroxide vapor; however, this is not preferred since sterilization times may be increased substantially due to the increase in time required for penetration of a sterilizing concentration of the vapor into the interstices of the bone or bone product. The bone tissue to be sterilized is also preferably free of blood and bone marrow because certain enzymes, such as catalase and other peroxidases present in substantial quantities in blood and marrow cells, degrade hydrogen peroxide into oxygen and water and could also compromise its effectiveness as a sterilant. Additionally, both fat and marrow fill the spaces of the cancellous bone and the medullary canal. If penetration of the hydrogen peroxide sterilant vapor into these spaces under vacuum conditions is desired, fat and marrow are preferably removed prior to exposure to the vacuum. If penetration of the vapor deeper than the cortical portion of the bone is not desirable or necessary, it may suffice to remove only surface blood and/or fat which may be present. An example of this is the surface sterilization of whole demineralized bone or bone segments, such as femoral heads, at slightly above or slightly below atmospheric pressure. Drying of the bone tissue prior to exposure to hydrogen peroxide vapor is also preferable, to prevent the potential for the dissolving of the vapor in moisture and a concomitant reduction in its effective concentration.

The bone tissue to be sterilized by the method of the invention is first processed, by known methods, to form a bone product suitable for transplantation. If vital bone proteins, such as bone morphogenetic proteins or osteogenesis factors, are to be preserved for inductive bone regeneration processes, the temperature at which the processing steps are carried out and the treatments employed in processing steps are preferably selected to prevent substantial denaturation of these proteins. For example, the processing temperature would be selected to be at or below physiological temperature, and cleaning with saline or water may be preferred instead of cleaning with detergents.

In general, the processing steps may include an optional preliminary decontamination step wherein the bone is treated, for example, with disinfectants and/or broad spectrum antibiotic solutions known in the art, followed by the step of debridement (the removal of soft tissue and cartilage attached to the bone). When debridement is completed, the bone may be shaped into various sized pieces for processing by using, for example, pneumatic drills and saws. The resulting pieces may include bone blocks, such as blocks of cancellous bone, or the bone may be ground into bone chips or pulverized into bone powder. A cleaning step may precede or follow the shaping step. Cleaning may be effected by conventional methods, such as contacting the bone with a detergent to remove fat, marrow and other debris, or by rinsing the bone with saline or pressurized water. The bone may be cleaned and decontaminated further by exposing it to a 0.5 to 10%, preferably 3%, hydrogen peroxide solution, which has bactericidal properties and also removes some marrow and/or fat. Defatting and dehydrating of the bone may also be effected by treating the bone with any suitable lipophilic and/or hydrophilic solvent, such as acetone, ethanol or ether. Dehydration may also take place during the step of lyophilization of defatted bone tissues.

Demineralization of the bone product may be effected by any known demineralizing agent, including but not limited to solutions comprising organic or mineral acids (such as formic acid, hydrochloric acid, nitric acid, citric acid, or oxalic acid) and/or calcium chelators such as ethylenediamine-tetracetate (EDTA). The demineralization step may serve to increase the porosity of the bone tissue.

If preservation of vital proteins is not important to the bone product, as for conductive bone regeneration wherein the product serves only a structural or matrix function, then during or following the process steps, the bone optionally may undergo a tanning process, for example by treatment with glutaraldehyde, prior to the terminal sterilization method of the instant invention.

Collagen preparations, suitable as transplants for either conductive or inductive bone regeneration, may be prepared by methods known in the art.

Following processing of the bone tissue into the final bone product for transplantation, the product may be sterilized by the method of the instant invention prior to or after its preservation by lyophilization, or prior to cryopreservation or fresh freezing.

In one embodiment of the invention, bone tissue, which has been processed by the previously described methods and has been defatted, is substantially free of moisture and blood and, preferably, has been demineralized, is exposed to a sterilant comprising hydrogen peroxide vapor. The vapor is generated by known means from any liquid containing hydrogen peroxide, such as peroxy compounds, including peracetic acid, or 6%–70% liquid hydrogen peroxide or, preferably, a 20–58% aqueous solution of hydrogen peroxide. Means for generating hydrogen peroxide vapor are known in the art, and typical methods and apparatus are disclosed, for example, in commonly owned U.S. Pat. Nos. RE.33007 and 5,068,087, the disclosures of which are hereby incorporated by reference. The processed bone tissue is exposed to the hydrogen peroxide vapor at a pressure, temperature, and concentration, and for a period of time sufficient to sterilize the bone tissue, but insufficient to cause substantial physical, chemical and biological damage to the bone tissue, such as undesirable excessive cross-linking of collagen and/or denaturation of essential proteins. Following exposure to the vapor hydrogen peroxide, the chamber and bone tissue undergo an aeration cycle, to remove substantially all residual hydrogen peroxide vapor from the chamber and bone tissue.

Sterilization of the bone tissue may be achieved by any sterilization method employing hydrogen peroxide vapor as the sterilant. Preferably, the sterilization temperature is between about 10° C. and about 45° C., and more preferably is about 30° C. The concentration of hydrogen peroxide vapor preferably ranges from about 0.5 mg/L to 10 mg/L; however, the preferred concentration of hydrogen peroxide vapor that will produce optimal sterilization without substantial condensation of the vapor can be determined by experimentation by one skilled in the art, based on certain variables, including the type and size of the bone tissue to be sterilized, the volume of the chamber, the chamber pressure, temperature and relative humidity and, if appropriate, the relative humidity and temperature of the inert carrier gas, and the flow rate of the carrier gas and vapor through the chamber. Similarly, the period of time sufficient to sterilize the bone tissue may vary depending on the type of bone and the particular application protocols for various samples, and can be established without undue experimentation.

In an embodiment of the invention, which may be useful if penetration into the tissue by the vapor is desired, the processed, defatted tissue is placed in a sterilization chamber and the chamber evacuated. This evacuation step removes substantially all residual moisture from the tissue. The tissue is then exposed to hydrogen peroxide vapor at a first subatmospheric pressure for a period of time sufficient to allow the vapor to diffuse into the interstices of the tissue. An inert gas, such as air, dry air, helium or nitrogen, with or without sterilant vapor, may then be introduced into the chamber to raise the pressure in the chamber to a second subatmospheric pressure to facilitate further penetration of the vapor into the tissue. After a short hold period, the chamber is re-evacuated and the steps of exposure, inert gas introduction (if used) and re-evacuation may be repeated until sterilization is achieved. The chamber is then aerated by known means to remove residual vapor from the chamber and the tissue. Such deep vacuum methods of sterilization with hydrogen peroxide vapor are disclosed in co-owned U.S. Pat. No. 4,956,145 and U.S. patent applications, Ser. No. 07/973,372, filed Nov. 12, 1992, now U.S. Pat. No. 5,527,508, and application Ser. No. 08/279,688, filed Jul. 25, 1994, now U.S. Pat. No. 5,492,672, the disclosures of which are hereby incorporated by reference.

In another embodiment of the invention, the bone tissue may be exposed to the hydrogen peroxide vapor in a "flow-through" chamber, such as an isolation chamber. In this sterilization cycle, surface-dry, preferably demineralized bone tissue, such as a whole bone or a section of bone, which is substantially free of surface blood and/or fat, is exposed to the sterilant at or slightly below or slightly above atmospheric pressure. Preferably the pressure is maintained within plus or minus 4 Torr of ambient pressure. A typical flow-through method includes the steps of introducing an inert carrier gas, such as air, dry air, helium, nitrogen, or mixtures thereof, into the chamber during the exposure step, and flowing the hydrogen peroxide vapor and carrier gas into, through and out of the chamber, while maintaining the chamber pressure and the concentration of hydrogen peroxide in the chamber. Such a method is disclosed in commonly owned U.S. Pat. Nos. 4,909,999 and 5,445,792, the disclosures of which are hereby incorporated by reference. Such a method may be preferred for bone tissue, such as femoral heads, in which substantial fat and bone marrow have not been removed and where subjecting such bone tissue to a substantial vacuum may detrimentally cause exudation of fat and bone marrow from the tissue, and comprise sterilization efficacy.

A combination of a deep vacuum method and flow-through method which may be used to sterilize the bone tissue in the instant invention is disclosed in U.S. Pat. No. 5,492,672, the disclosure of which has been previously incorporated.

In another embodiment of the method of the invention, a bone tissue such as, but not limited to, cancellous bone block, bone chips, bone powder, or a collagen preparation is processed according to the methods previously described, and is preferably demineralized, substantially defatted, and is substantially free of blood and/or bone marrow. The bone tissue is placed into a loosely capped container, which is then placed into a lyophilization chamber and the tissue is lyophilized by known methods. The vacuum achieved in the chamber during lyophilization (typically between about 200 microns and about 200 Torr) is sufficient to substantially dehydrate the bone tissue. When lyophilization is complete, the lyophilized bone tissue in the loosely capped container may be transferred to a sterilization chamber for sterilization by hydrogen peroxide vapor, by methods as described above.

Alternatively and preferably, the evacuated lyophilization chamber also serves as the sterilization chamber. In this embodiment, the evacuated lyophilization chamber is isolated from the condenser by valve means prior to the introduction of hydrogen peroxide vapor into the chamber. The lyophilized tissue is then exposed to hydrogen peroxide vapor in sterilization pulses which sequentially introduce sterilant vapor into the chamber for a predetermined period of time, admit a filtered flow of inert gas, preferably air, into the chamber for another period of time to reach a higher subatmospheric pressure and then re-evacuate the chamber prior to repeating the sterilization pulse. A typical sterilization cycle for sterilization of the chamber and condenser of a lyophilizer is described in co-pending, co-owned U.S. patent application Ser. No. 08/450,931, filed May 24, 1995, the disclosure of which is hereby incorporated by reference, and is a suitable and preferable sterilization cycle for sterilization of the lyophilized product. Following the sterilization pulses, the chamber is aerated by known means to remove residual hydrogen peroxide from the chamber and the bone tissue product.

The following is an illustrative example of the present invention as applied to two different bone tissue samples. The microbial flora which may contaminate the bone tissue prior to sterilization is believed to comprise mainly vegetative cells. However, for purposes of illustration of the sterilization capabilities of the hydrogen peroxide vapor as utilized in the present invention, bone tissue was contaminated experimentally with one of the most resistant microbial forms for this method of sterilization, i.e. *Bacillus stearothermophilus* spores.

EXAMPLE

Frozen human femoral bone was thawed for 3 hours until it reached room temperature. Preliminary decontamination was performed using an antibiotic cocktail of polymyxin B and bacitracin in Minimal Essential Medium. The bone was debrided, cut into pieces, and rinsed with pressurized water. Twelve pieces of cancellous bone and one piece of cortical bone, with dimensions of about 5 mm. ×5 mm. ×5 mm., were selected and immersed in several changes of a 3% liquid hydrogen peroxide for about 20 minutes, or until bubbling ceased, followed by rinsing with pressurized water. The bone was then immersed in 70% ethyl alcohol for 24 hours, followed by lyophilization.

Twelve pieces of the treated cancellous bone and one piece of treated cortical bone were then contaminated by placing 0.010 mL of a 1×10$^6$/mL suspension of *Bacillus stearothermophilus* on each bone piece. The bone pieces were held at room temperature for 30 minutes or until the suspension had completely dried. One piece of cancellous bone was not contaminated, and served as a negative control. Another piece of cancellous bone was contaminated but not subjected to sterilization, and served as a positive control.

Ten cancellous and one cortical contaminated bone pieces were then placed in a hydrogen peroxide sterilization chamber, and exposed to about 3.5 mg/L hydrogen peroxide vapor in a constant flow-through with air at atmospheric pressure and room temperature during twelve-minute exposure pulses, followed by an aeration cycle. The hydrogen peroxide vapor was generated from a 31% reagent grade solution of hydrogen peroxide. Bone piece samples were removed from the chamber after sterilization cycles comprising 3 or 4 or 5 exposure pulses. After sterilization, the bone pieces were placed in trypticase soy broth culture media and incubated for two weeks. At the end of the incubation period, the positive control samples showed bacterial growth. However, none of the inoculated, exposed samples showed bacterial growth. Therefore, both cancellous and cortical bone tissue were sterilized by exposure to hydrogen peroxide vapor in as few as three 12-minute exposure pulses.

While the invention has been described herein with reference to the preferred embodiments, it is to be understood that it is not intended to limit the invention to the specific forms disclosed. On the contrary, it is untended to cover all modifications and alternative forms falling within the spirit and scope of the invention.

We claim:

1. A method of sterilization of bone tissue comprising:
   a) inserting bone tissue which is substantially defatted and substantially free of moisture and blood in a chamber;
   b) exposing the defatted and substantially moisture and blood free bone tissue to hydrogen peroxide vapor at a subatmospheric pressure, temperature, and concentration, and for a period of time sufficient to sterilize the bone tissue to a sterility assurance level of 10$^{-6}$, but insufficient to cause substantial physical, chemical, and biological damage to the bone tissue; and
   c) removing substantially all residual hydrogen peroxide vapor from the chamber and the bone tissue.

2. The method according to claim 1, further including before step (a) demineralizing the bone tissue.

3. The method according to claim 1, wherein the bone tissue comprises lyophilized bone tissue.

4. The method according to claim 1, further including lyophilizing the defatted and substantially moisture and blood free bone tissue in the chamber.

5. The method according to claim 1, wherein the bone tissue is selected from the group consisting of whole bone, sections of whole bone, bone chips, bone powder, tanned bone, collagen preparations and mixtures thereof.

6. The method according to claim 1, wherein the bone tissue is selected from the group consisting of cancellous bone tissue, cortical bone tissue, and mixtures thereof.

7. The method according to claim 1, wherein the hydrogen peroxide vapor is generated from the group consisting of liquid hydrogen peroxide and peroxy compounds.

8. The method according to claim 7, wherein the hydrogen peroxide vapor is generated from liquid hydrogen peroxide, wherein the liquid hydrogen peroxide comprises a 20–58% aqueous solution.

9. A method of sterilization of bone tissue comprising:
   a) placing bone tissue which is substantially defatted and substantially free of moisture and blood in a chamber;
   b) reducing the pressure in the chamber to a first subatmospheric pressure;
   c) exposing the bone tissue to hydrogen peroxide vapor sterilant at a pressure, temperature, and concentration, and for a period of time;
   d) introducing an inert gas into the chamber after the exposure step to raise the pressure in the chamber to a second subatmospheric pressure;
   e) re-evacuating the chamber; and
   f) repeating steps (b), (c), (d), and (e) until sterilization is achieved; and
   g) removing substantially all residual hydrogen peroxide vapor from the bone tissue.

10. A method of sterilization of bone tissue comprising:
    a) placing bone tissue having an outer cortical layer and an inner cancellous layer in a chamber, said tissue having a substantially dry, substantially blood-free surface;
    b) exposing the bone tissue to hydrogen peroxide vapor sterilant at near atmospheric pressure, and at a temperature, concentration, and for a period of time sufficient to sterilize the cortical layer but insufficient to substantially penetrate the cancellous layer of the bone tissue; and
    c) removing substantially all residual hydrogen peroxide vapor from the chamber and the bone tissue.

11. The method according to claim 10, further comprising the steps of introducing an inert carrier gas into the chamber during the exposure step; and flowing the hydrogen peroxide vapor and carrier gas into, through and out of the chamber, while maintaining the pressure and the concentration of hydrogen peroxide in the chamber.

12. The method according to claim 10, wherein the pressure is between about ambient pressure plus 4 Torr and about ambient pressure minus 4 Torr.

13. The method according to claim 10, wherein the bone tissue comprises an entire bone or a cut section thereof.

14. The method according to claim 13, wherein the bone tissue comprises a femoral head.

15. The method according to claim 10, wherein the hydrogen peroxide vapor is generated from the group consisting of liquid hydrogen peroxide and peroxy compounds.

16. The method according to claim 15, wherein the hydrogen peroxide vapor is generated from liquid hydrogen peroxide, wherein the liquid hydrogen peroxide comprises a 20–58% aqueous solution.

17. A method of sterilization of bone tissue comprising:
   a) demineralizing bone tissue having an outer cortical layer and an inner cancellous layers said tissue having a substantially dry, substantially blood-free surface;
   b) placing the demineralized bone tissue in a chamber;
   c) exposing the demineralized bone tissue to a hydrogen peroxide vapor sterilant at a pressure, temperatures, concentration, and for a period of time sufficient to sterilize the cortical layer, but insufficient to substantially penetrate the cancellous layer of the bone tissue; and
   d) removing substantially all residual hydrogen peroxide vapor from the bone tissue.

18. A method of final sterilization of bone tissue consisting of the following steps:
   a) inserting bone tissue which has been substantially defatted and substantially free of moisture and blood into a chamber;
   b) exposing the bone tissue to a hydrogen peroxide vapor sterilant at a subatmospheric pressure, temperature, and concentration, and for a period of time sufficient to sterilize the bone tissue and provide a sterility assurance level of $10^{-6}$, but insufficient to cause substantial physical, chemical, and biological damage to the bone tissue;
   c) removing substantially all residual hydrogen peroxide vapor from the chamber and the bone tissue.

19. A method of final sterilization of bone tissue consisting of the following steps:
   a) placing bone tissue having an outer cortical layer and an inner cancellous layer in a chamber, said tissue having a substantially dry, substantially blood-free surfaces;
   b) exposing the bone tissue to hydrogen peroxide vapor sterilant at near atmospheric pressure, and at a temperature, concentration, and for a period of time sufficient to sterilize the cortical layer, but insufficient to substantially penetrate the cancellous layer of the bone tissue;
   c) removing substantially all residual hydrogen peroxide vapor from the chamber and the bone tissue.

* * * * *